United States Patent [19]
Spitler et al.

[11] Patent Number: 5,925,362
[45] Date of Patent: *Jul. 20, 1999

[54] METHOD TO ELICIT AN ANTITUMOR RESPONSE WITH HUMAN PROSTATE-SPECIFIC ANTIGEN

[75] Inventors: Lynn E. Spitler, Tiburon; Anthony E. Maida, III, Danville, both of Calif.

[73] Assignee: Jenner Technologies, San Ramon, Calif.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/288,057

[22] Filed: Aug. 10, 1994

Related U.S. Application Data

[63] Continuation-in-part of application No. 08/105,444, Aug. 11, 1993.

[51] Int. Cl.⁶ ............................ A61K 35/48; A61K 48/00
[52] U.S. Cl. ..................................... 424/277.1; 424/184.1; 424/520; 424/559; 424/812; 424/93.2; 424/450; 514/44
[58] Field of Search ............................. 424/130.1, 131.1, 424/138.1, 141.1, 152.1, 184.1, 193.1, 277.1, 520, 93.2; 435/320.1; 530/350, 387.2

[56] References Cited

U.S. PATENT DOCUMENTS

| | | |
|---|---|---|
| Re. 33,405 | 10/1990 | Chu et al. ............................. 530/350 |
| 3,960,827 | 6/1976 | Bjorklund . |
| 4,372,945 | 2/1983 | Likhite . |
| 4,446,122 | 5/1984 | Chu et al. . |
| 4,468,457 | 8/1984 | Goldenberg et al. . |
| 4,689,222 | 8/1987 | McMichael . |
| 4,877,611 | 10/1989 | Cantrell . |
| 5,053,224 | 10/1991 | Koprowski et al. . |

FOREIGN PATENT DOCUMENTS

| | | |
|---|---|---|
| WO91/11465 | 8/1991 | WIPO . |
| 9804727 | 2/1998 | WIPO . |

OTHER PUBLICATIONS

Murphy et al. The Prostate 29:371–380 (1996).
Salgaller et al. Proc Am Assoc Cancer Res 38:616 (1997).
Tsang et al. JNCI 87:982–990 (1995).
Wright et al. Int. J. Cancer 47:717–725 (1991) Abstract Only.
Beckett et al. Cancer Res. Search 51:1326–1333 (1991) Abstract Only.
Hodge et al. Int. J. Cancer 63:231–237 (1995).
Spitler et al. Cancer Biotherapy 10:1–3 (1995).
Ezzell J NIH Research 7:46–49 (1995).
Vieweg et al. Cancer Research 54:1760–1765 (1994).
Linehan et al. JNCI 87:331–332 (1995).
Boring, CC, et al, Cancer Statistic, 1993:*CA Cancer J Clin* (1993) 43:7–26.
Hoover, Jr. HC and Hanna, Jr. MG, *Biological Therapy of Cancer* (1991) Devita, Jr., DT, et al., Biologic Therapy of Cancer; eds. J.B. Lippincott Co., pp. 670–701.
Deguchi et al., Effect of Methotrexate–Monoclonal Anti–Prostatic Acid Phosphatase Antibody Conjugate on Human Prostate Tumor, Cancer Research 45:3751–3755.
Alving, C.R., Liposomes as Carriers of Anitgens and Adjuvants, J. Imunol. Methods 140:1–13 (1990).
Faseb, J., Generation and Characterization of Monoclonal Anti–Idiotypic Antibodies for Dunning Rat Prostate Tumor, Abstract No. 2301; A692 entire abstract (1988).

*Primary Examiner*—Christina Y. Chan
*Assistant Examiner*—Phillip Gambel
*Attorney, Agent, or Firm*—Morrison & Foerster LLP

[57] ABSTRACT

Vaccines capable of eliciting an immune antitumor response for prostate tumors are disclosed. The active ingredient in such vaccines is selected from the group consisting of human PSA and expression system capable of generating in situ human PSA.

8 Claims, No Drawings

METHOD TO ELICIT AN ANTITUMOR RESPONSE WITH HUMAN PROSTATE-SPECIFIC ANTIGEN

This is a Continuation-In-Part of U.S. Ser. No. 08/105,444 filed Aug. 11, 1993 now pending. The contents of this application are incorporated herein by reference.

TECHNICAL FIELD

The present invention is related to the field of the prevention and treatment of prostate cancer. More specifically, the invention concerns the use of (1) prostate associated antigen(s), (2) expression systems for prostate associated antigen(s) which are peptides or proteins or (3) anti idiotypic antibodies bearing the internal image of the antigen(s) formulated as vaccines to produce an immune response to prevent or treat prostate cancer.

BACKGROUND ART

Cancer is the second leading cause of death in the United States accounting for almost 500,000 deaths each year. More than 1,000,000 new cases of cancer are diagnosed in the United States annually. The incidence of cancer is increasing largely as a byproduct of the greater lifespan of the aging population. Cancer is a leading cause of death in all industrialized nations, where life expectancy continues to increase. It is expected that cancer morbidity and mortality will continue to increase in all industrialized areas of the world.

Prostate cancer is the most common malignancy among males in the U.S. accounting for 28% of all malignancies in men. It is estimated there will be 165, 000 new cases of prostate cancer in the United States in 1993 and 35,000 deaths (Boring, CC, et al *CA Cancer J Clin* (1993) 43:7–26).

Prostate cancer continues to be refractory to treatment despite many years of efforts to improve therapy. Surgery and radiation remain the mainstays of therapy; improved therapeutic modalities are needed. Vaccine development has been slow and no vaccine approved by the FDA for marketing currently exists for any form of cancer. There is therefore a continuing need for the development of new therapeutic and prophylactic compounds effective in the prevention and treatment of prostate cancer The use of vaccines as cancer therapy is known (reviewed in Hoover, Jr. HC and Hanna, Jr. MG, *Biological Therapy of Cancer* (1991) Devita, Jr., DT, et al., eds. J. B. Lippincott Co., pp 670–701. There are many reports in the open literature of vaccines consisting of whole autologous or allogeneic tumor cells or their extracts formulated with bacterial adjuvants such as Bacillus-Calmette-Guerrin (BCG), *Corynebacterium parvum* or vaccinia virus. There has been no report of the use of an antigen unique to the prostate such as a prostate associated protein or an anti idiotypic antibody bearing the internal image of the prostate antigen as a vaccine for prostate cancer.

U.S. Pat. No. 3,960,827 describes a cancer-associated polypeptide antigen which is described as having a molecular weight of 20–27 kd and as associated with a number of types of cancers. The use of this antigen in antitumor vaccines is suggested. U.S. Pat. No. 4,372,945 discloses the use of tumor cells as secondary antigens in immunotherapeutic treatment of cancer. U.S. Pat. No. 4,446,122 discloses the use of prostate specific antigen (PSA) isolated from human tissue to prepare antibodies for tumor diagnosis. U.S. Pat. No. 4,468,457 describes the isolation of a colon specific antigen which is digested with trypsin to obtain a peptide used to produce monospecific antibodies against the antigen. U.S. Pat. No. 4,689,222 describes a method for alleviation of symptomatic pain associated with neoplasia by administering a low dose of human chorionic gonadotropin insufficient to provoke a humoral response. U.S. Pat. No. 4,877,611 describes vaccines containing tumor-associated antigens. The vaccines contain the tumor-associated antigen in the presence of specific adjuvants. PCT application WO91/11465 describes anticancer vaccines using antiidiotype antibodies that mimic an antigen produced by or associated with the malignant cell.

U.S. Pat. No. 5,053,224 issued Oct. 1, 1991 describes the preparation of both polyclonal and monoclonal anti idiotypic antibodies that recognize the paratope of an antitumor antibody. The issued patent further describes the use of these anti idiotypic antibodies generally to stimulate the production of anti anti idiotypic antibodies in tumor patients. Copending patent application No. 07/938,079 filed Aug. 31, 1992, now abandoned in favor of File Wrapper Continuation Ser. No. 08/185,313 filed Jan. 21, 1994 the disclosure of which is incorporated herein by reference discloses the use of anti idiotypic antibodies generally to stimulate an antitumor T cell response for prevention and/or therapy of cancer. Copending patent application No. 07/800,474 filed Nov. 26, 1991, now abandoned in favor of File Wrapper Continuation Serial No. 08/151,568 filed Nov. 12, 1993 the disclosure of which is incorporated herein by reference describes generally the use of pure tumor antigen encapsulated in or conjugated to liposomes for the treatment and prevention of cancer.

The present invention concerns the use of prostate antigens or their representatives in vaccines to produce an immune response to prevent or treat prostate cancer.

DISCLOSURE OF THE INVENTION

While the prior art suggests the use of antigens uniquely associated with tumor tissue as components of antitumor vaccines, there appears to be no suggestion to use antigens which are uniquely represented on host tissue for the tumor. Since the prostate is not an essential organ, elimination of the prostate gland, which may be a concomitant effect of the vaccines of the invention, does not adversely impact the general health of the subject. Thus, prostate cancer offers a unique opportunity for treatment with vaccines which characterize the host organ itself, rather than the malignant or metastatic nature of the cells per se.

Accordingly, in one aspect, the invention is directed to a method to induce an antitumor immune response in a potential or actual prostate tumor-bearing subject which method comprises administering to said subject a composition comprising an active ingredient selected from the group consisting of at least one antigen over-represented in the prostate gland or an immunologically effective portion thereof; an expression system capable of generating in situ said antigen; and an anti idiotypic antibody or fragment thereof which mimics said antigen.

In another aspect, the invention is directed to a pharmaceutical or veterinary vaccine for eliciting an antitumor immune response to prostate tumors which comprises, as active ingredient, at least one antigen over-represented on the prostate gland with respect to other tissues or an immunologically effective portion thereof; or an expression system capable of generating in situ said antigen; or an anti idiotypic antibody or fragment thereof which mimics said antigen.

MODES OF CARRYING OUT THE INVENTION

The invention utilizes compositions which contain, as active ingredient, at least one antigen which is over-represented on prostate tissue or an immunologically effective portion thereof or a representative thereof. By "over-represented" is meant that the concentration of this antigen in prostate is sufficiently higher than its concentration in any other tissue such that the prostate can effectively be targeted by the immune response raised against this antigen with relative sparing of other organs or tissues. Sparing can be measured by overall clinical toxicity to the subject. Toxicity to the subject is generally grade 3 or less, preferably grade 2 or less most preferably grade 1 or grade 0. The approach does not lose value with regard to metastatic prostate cancer, since the antigens over-represented in the prostate gland are also carried by the metastatic cells.

By an "immunologically effective portion thereof" is meant that portion of an antigen, taken alone, which is capable of eliciting an immune response. Typically, such portions represent an individual epitope or a specific subset of the epitopes that comprise the complete antigen.

The antigen can be any substance which is, in the sense used above, unique to or over-represented in prostate tissue. Thus, the antigen may be a protein or a peptide, or peptide fragment of the protein, or may be a carbohydrate, glycoprotein, lipoprotein or lipid. Most commonly, the antigen will be a protein or a peptide fragment thereof; or a protein which includes the amino acid sequence of the antigen or epitope. Proteins may be modified by glycosylation or other derivatization. It is clear that in the case of protein antigen, peptides representing epitopes of the antigen may also be used, The relevant amino acid sequence can be supplied in the context of a larger fusion protein that contains amino acid sequence heterologous to the antigen or its epitope.

It is also understood that in the case of peptide or protein antigens, the antigens may be generated in situ by providing suitable expression systems containing the DNA encoding the desired peptide or protein (including fusion proteins containing the relevant sequence); the expression systems can then be used as the active ingredient in the vaccines. By "expression system" is meant any DNA construct which is effective in producing the encoded protein in the desired environment. Conventional expression systems contain the encoding DNA operably linked to control sequences such as promoters, terminating signals and the like. However, it has recently been shown that the coding sequences per se can behave as effective expression systems in situ when injected into animals. The work of Ulmer, J. B., et al., *Science* (1993) 259:1745–1749, and summarized in a "Research News" presentation by Cohen, J., in the same issue on pages 1691–1692 demonstrates this concept. Injection of "naked" DNA encoding the nucleoprotein of influenza A was shown to be protective against a challenge of the virus. Although it is not understood why such naked DNA is apparently capable of expression to provide the protein in situ, this apparently is the case. Accordingly, such "naked" DNA is included in the definition of expression systems herein.

Furthermore, any antigen may be mimicked by an anti idiotypic antibody; it has long been recognized that anti idiotypic antibodies can be prepared that bear an internal image of tumor associated antigens, (Herlyn, D., et al. *Science* (1986) 232:100–102.

Illustrative Antigens

The first widely studied antigen which is over-represented in the prostate gland is prostatic acid phosphatase (PAP). Elevated levels of PAP in the bloodstream are considered indicative of prostate cancer, and this enzyme has been widely studied (Yam, *Amer J Med* (1974) 56:604. Improved methods of cancer detection using this enzyme were described by Chu et al. in PCT application WO79/00475. The structure of the enzyme has also been studied by Sharief, F. S., et al., *Biochem Biophys Res Commun* (1992) 184:1468–1476 and by Van Etten, R. L., et al., *J Biol Chem* (1991) 266:9993–9999. The nucleotide sequence encoding human PAP has been determined from a full length cDNA clone (Sharief, F. S., et al., *Biochem Biophys Res Commun* (1989) 180:79–86; Tailor, P. G., et al., *Nucleic Acids Res* (1990) 18:4928.

In addition to PAP, other suitable candidates for antigens over-represented on prostate tissue are known. Most prominent among these is "prostate specific antigen" or "PSA".

U.S. Pat. No. 4,446,122 discloses methods for the purification of human prostate specific antigen (PSA) from either normal or cancerous human prostate tissue, prostatic fluid, cultured human prostatic malignant cells, or their media. Also disclosed are polyclonal and monoclonal antibodies to the prostate specific antigen and their use in a method for diagnosing carcinoma of the prostate. PSA is a member of the glandular kallikrein family and is a protease with a restricted chymotrypsin-like specificity; it is present in the epithelial cells comprising the prostatic ductal elements. It has been demonstrated in all primary and metastatic prostatic tumors tested and in normal benign prostate but not in nonprostatic cancer tissues or in normal tissues other than prostate.

The complete amino acid sequence of PSA from human seminal plasma has been determined (Watt KW et al., *Proc Natl Acad Sci USA* (1986) 83:3166–3170). PSA consists of a single polypeptide chain with 240 amino acid residues and has a calculated molecular weight of 26,496. Carbohydrate side chains are possibly attached. The cDNA encoding PSA has been produced and characterized (Lundwall A, Lilja, H, *FEBS Lett* (1987) 214:317–322; Schultz P, et al., *Nucleic Acids Res* (1988) 16:6226; and Henttu P and Bihko P, *Biochem and Biophys Res Commun* (1989) 160:903–910). The gene for the PSA has also been characterized (Lundwall A, *Biochem and Biophys Res Commun* (1989) 162:1151–1159, Riegman, PHJ, et al., *Biochem and Biophys Res Commun* (1989) 159:103–111 and Klobeck G, et al., *Nucleic Acids Res* 1989 17:3981.)

cDNA encoding a different prostate specific membrane antigen (PSMA) has also described (Israeli RS et al., *Cancer Res* (1993) 53:227–230). The cDNA consists of 2.65 kilobase and a portion of the coding region from nucleotide 1250 to 1700 has 54% homology to the human transferrin receptor mRNA. In contrast to PSA and prostatic acid phosphatase which are secreted proteins, the prostate specific membrane antigen is an integral membrane protein.

The PSMA (molecular weight 100,000) similarly has representation on both benign and neoplastic prostate cells with more intense staining seen with malignant cells. Metastases of prostate cancer also have representation of the antigen. This antigen, therefore, is an appealing as a vaccine candidate for the same reasons as those described for PSA. Moreover,PSMA is an integral membrane protein rather a secreted protein as is PSA ,and, therefore, may be an even more appropriate vaccine component.

The foregoing list of known antigens which are over-represented on prostate: prostatic acid phosphatase (PAP); prostate specific antigen (PSA); and prostate specific membrane antigen (PSMA) is offered for the purpose of illustration. These well known antigens (or the epitope bearing fragments thereof) are proteins (or peptides) and are useful in the vaccines of the invention. However, the invention includes any other antigens substantially uniquely present on the prostate gland so that prostate derived tissue can be distinguished from other tissue by virtue of the presence of these antigens.

Preparation of the Antigens

Antigens useful in the vaccines may be prepared by any suitable methods. The antigens may be isolated and purified from prostatic tissue using conventional methods. The purification of the representative antigens set forth above is already known, and art-known techniques for their purification may be employed. In addition, affinity columns employing antibodies or fragments thereof for specific adsorption of the desired antigen can be used to advantage. The nature of the purification method will, of course, depend on the nature of the antigen obtained.

For antigens that are proteins or peptides, a number of options is available in addition to isolation and purification. In addition to genetic engineering techniques, peptides, and even proteins, can be prepared using standard chemical synthesis methods, preferably the commercially available solid-phase-based techniques. These techniques are well known and automated systems to conduct them can be purchased and employed according to the manufacturer's instructions.

In addition, protein or peptide antigens may be prepared using genetic engineering. Procedures for the production of pure antigens from the DNA encoding the desired antigen are well known to those skilled in the art. Briefly, the preferred DNA is expressed in a suitable recombinant expression vector such as those adapted for *E. coli*; yeast, such as *Saccharomyces cerevisiae* or *Pichia pastoris*; or filamentous fungi such as *Aspergillus nidulans*. The yeast, fungi or bacteria, can be grown in continuous culture producing recombinant protein which may be then be isolated and purified. Alternately, higher organisms may be used for recombinant protein production. For example, the encoding DNA may be expressed in an insect virus expression vector such as recombinant baculovirus and the resulting recombinant baculovirus then used to infect susceptible cultured SF9 cells (*Spodotera frugiperda* insect cells) to produce the protein product of the DNA. Other expression systems commonly used include those appropriate for production of proteins in mammalian cells, such as CHO cells or even plant cells. The choice of host will determine the nature of the posttranslational processing, and is a consideration in devising purification techniques.

The preparation of recombinant forms of protein antigens in a variety of host cells results in a variety of posttranslational modifications which affect the immunogenicity and other pharmaceutical properties, such as pharmacokinetics, of the product. Accordingly, although human prostate-specific antigen (PSA) isolated from human tissues has been used to induce the production of antibodies for diagnostic use, the immunogen prepared in this way differs from the immunogen as prepared in nonhuman cells, such as insect cells. The posttranslational modifications peculiar to the recombinant host result in alternations in glycosylation pattern, folding, and the like.

The technique of recombinant expression may also be used to produce portions of the desired antigen rather than the entire antigen. For example, it maybe desirable to express the extracellular domain without the intracellular and/or transmembrane domains to facilitate purification of membrane associated antigen. Similarly, it may be desirable to express just the epitopes of choice eliminating unrelated or competing epitopes. All of these may be accomplished through techniques well known to those skilled in the art. Techniques for identifying peptides representing important epitopes of the antigen are well known, and are summarized in Berzofsky, JA and Berkower IJ, *Fundamental Immunology* 2nd edition, Raven Press, (1989) W. E. Paul (ed.) pp. 169–208. The peptides identified may then be synthesized using conventional solid phase peptide synthesis (Merrifield RB, *J Am Chem Soc* (1983) 85:2149–2154) which has now been automated (Merrifield RB, *Science* (1965) 150:178–185) as described above. An alternate method designed to make large numbers of peptides for screening is the "tea-bag" technique (Houghten RA, *Proc Natl Acad Sci USA* (1985) 82:5131–5135.

Whether the antigen or a suitable epitope is prepared synthetically or recombinantly, it may be prepared initially as a fusion protein containing amino acid sequence heterologous to the amino acid sequence of interest. Construction of such fusion proteins is common in recombinant production in order to stabilize the product produced in the cell. It may be unnecessary to stabilize the desired peptide or protein in this way, especially if it is to be secreted from the recombinant cell. However, the fusion protein itself may be useful as an ingredient in the vaccine, especially if the additional heterologous amino acid sequence supplies an immunogenicity enhancing property on the relevant epitope. Thus, the fusion proteins which contain the relevant amino acid sequences may be used simply as precursors of the immunogen or may provide the end-product for use in the vaccine. If the fusion protein is intended as an intermediate, it is useful to provide a cleavage site between the heterologous portion and the desired epitope. Such cleavage sites include, for example, the target sequences for various proteolytic enzymes, or, if the epitope does not contain methionine, may constitute simply a methionine residue which is cleaved by cyanogen bromide. Methods to provide suitable cleavage sites are well known in the art.

Preparation of Antiidiotypic Antibodies

An alternative approach in formulating the vaccines of the invention is to prepare a "representative" of the antigen in the form of an anti idiotypic antibody which bears an internal image of the antigen. Anti idiotypic antibodies can be prepared with respect to antigens of any chemical nature, including, in addition to peptides and proteins, carbohydrates, lipids, and small molecules.

Ways to prepare both monoclonal and polyclonal anti idiotypic antibodies which bear the internal image of the tumor associated antigens is described in detail in U.S. Pat. No. 5,053,224 the disclosure of which is incorporated herein by reference. Briefly, polyclonal anti idiotypic antibodies may be produced by immunizing animals with monoclonal idiotypic antibodies raised against the antigen and screened for reactivity with the antigen and screening for antisera which react with idiotypic antibodies to the prostate antigens. Monoclonal antibodies may also be prepared from such animals using standard techniques of immortalizing the antibody secreting cells of the animal and screening the cultures with idiotypic antibodies in competition with the prostate antigen. Human or murine monoclonals are preferred; polyclonal preparations made in a variety of mammalian systems may also be used.

Vaccine Compositions

While the prostate antigens of the invention may by themselves constitute the vaccine, it is a further feature of the invention these prostate antigens are administered in a formulation designed to enhance the antitumor response. Formulations include but are not limited to incorporation of the prostate antigen into a liposome with or without out additional adjuvants, use of adjuvants and/or cloning DNA encoding of peptide or protein antigens into a viral or bacterial vector.

Of course, the formulations may not contain only a single active ingredient; any combination of the immunogenic substances of the invention can be used.

However, generally, such "cocktails" comprise active ingredients of the same type—i.e., generally the active ingredient mixture will include either two or several antigens, two or several expression systems for protein or peptide antigens, or two or several anti idiotypic antibodies representing different antigens. However, there is no theoretical reason that, for example, a single vaccine could not include both anti idiotypic antibody and an expression system.

If the protein form of the antigen is to be used, it may be desirable to couple the protein or peptide to a carrier in order to enhance immunogenicity. Such coupling can be effected using standard and conventional coupling techniques, optionally utilizing spacer moieties in order to provide correct juxtaposition of the carrier and epitope. A large number of suitable carriers for such purposes is known, including keyhole limpet hemocyanin, rotavirus VP6 inner capsid protein, pilin protein and the like. In addition, enhanced immunogenicity may be obtained by supplying the epitope or antigen in the form of a fusion protein wherein the epitope bearing portion is fused to heterologous amino acid sequences to enhance the effect of the epitope administered.

Whether administered alone, coupled to carrier, or as part of a fusion protein, the epitope bearing proteins of the invention, the DNA constructs and the anti idiotypic antibodies are administered in the presence of suitable excipients. Conventional excipients may be used, but the following are of particular interest.

Compositions employing liposomes encapsulating or conjugating to the active ingredient of the vaccine may be used and are especially preferred. Liposomes localize in the reticuloendothelial system, one of the sites of generation of the immune response in a mammalian host including humans and enhance the immune response to antigens incorporated in the liposome The liposomal formulations incorporating the prostate antigens may also include immune system adjuvants, including one or more of lipopolysaccharide (LPS), lipid A, or muramyl dipeptide (MDP) as described in *Liposomes*, Ostro MJ, Editor, Marcel Dekker, Inc. (1983) page 249). Other immune system adjuvants such as glucan or certain cytokines, including interleukins, interferons, and colony stimulating factors, such as IL1, IL2, gamma interferon, and GM-CSF may also be incorporated with antigen into the liposome.

The prostate antigen may also be formulated with various adjuvants which enhance antitumor response, in particular, cellular immune response to the prostate antigens. Such adjuvants include, but are not limited to, Freund's Complete Adjuvant, alum, lipid A, monophosphoryl lipid A, Bacillus-Calmette-Guerin (BCG) and other bacteria, polysaccharides such as glucan, acemannan, and lentinan, saponins, detoxified endotoxin (DETOX), muramyl tripeptide, muramyl dipeptide and their derivatives, SAF1, lymphokines and cytokines, including interleukins and interferons such as IL2 and gamma interferon, as well as colony stimulating factors such as GM-CSF, nonionic block copolymers, or immune stimulating complexes (ISCOMS).

In an additional formulation the DNA encoding proteins such as PAP, PSA, PSMA, or portions of these is administered in a viral expression vector such as vaccinia or other pox virus or bacterial vectors such as BCG. Viral vectors are described, for example, by Hruby, D E, *Vet Parasitol* (1988) 29:281–282, and by Uiu, SI "AIDS Research Reviews" Dekker, Inc. (1991) 1:403–416. The recombinant vectors may be administered in the traditional manner via a skin scratch or an injection or may included in a liposome injectable as described above. As noted above, "naked" DNA can also be used as a form of expression system in the vaccines of the invention.

Administration and Use

In the method of the invention, the prostatic cancer vaccine is administered for both prevention and treatment of prostatic cancer. The prostatic cancer vaccine of the invention is administered to subjects at risk for the development for the development of prostate cancer or showing a diagnosis thereof. While the target cancer is specifically that associated with the prostate gland, the effect of the vaccines of the invention will be to enhance the potential of the immune system generally, generating T cell responses as well as the production of antibodies. To the extent that the enhancement of the cellular immune system is effected, the vaccines of the invention are useful in the prevention and therapy of other types of cancer as well as that of the prostate. Thus, the cellular responses generated are effective against, for example, cancers of the colon, lung, bladder, stomach, breast, cervix, and the like as well as certain lymphomas and leukemias.

The compositions are formulated for parenteral administration using a formulation appropriate to the administration route such as those described in *Remington's Pharmaceutical Sciences*, latest edition, Mack Publishing Company, Easton, Pa.

Suitable routes for parenteral administration include intracutaneous, subcutaneous, intramuscular, and intravenous injection or oral administration. For formulation for injection, the vaccine is generally formulated in a suitable liquid such as Hank's solution or Ringer's solution along with suitable excipients providing buffering, stabilizing, and other desirable characteristics, as well as additional components desired, as described below. Alternative routes for parenteral administration include oral administration in which case additional components for stabilizing the preparation may also be included.

In addition to administration in an appropriate isotonic vehicle for injection, liposomes are desirably used as a carrier to direct the product to the immune system as disclosed in copending application 07/800,474, the disclosure of which is incorporated herein by reference.

In general, the dosage range for the prostate antigens of the invention is of the order of 0.01 $\mu$g-100 mg per dose, preferably 0.1 $\mu$g-10 mg per dose and more preferably 10 $\mu$g-1 mg per dose. Suitable volumes for parenteral administration are about 0.1–5 ml.

The protocols may involve administration of cocktails of various antigens or their representatives or may involve sequential administration of these active ingredients. The antigens and their representatives may represent a variety of immunogens or may represent different forms of the same immunogen. In general, protocols involving one or more immunogenic species can be designed according to routine optimization procedures.

The prostatic cancer vaccine of the invention is administered generally in multiple doses, typically once per week for one or two months and with decreasing frequency thereafter for a period extending to about one year. Following the initial one year course of vaccination, booster inoculations may be given every two months to five years. Alternate protocols may be appropriate in individual instances. For example, if vaccine formulation involves the use of liposomes and is administered intramuscularly, the vaccine might be administered once a month from the inception because of the depot effect of the liposomes.

In addition, it may be advantageous to substitute for the first administrations a recombinant form of the antigen wherein the antigen gene or cDNA is administered in a living expression vector such as vaccinia virus.

It is a further feature of the invention that the vaccine may be formulated along with adjuvants which enhance the immune responses as described above. The prostate antigens may be formulated with these adjuvants alone or they may be incorporated into liposomes.

We claim:

1. A method to elicit an antitumor immune response to prostate tumors in a subject which comprises administering to said subject at least one active ingredient formulated for administration to said subject, wherein said active ingredient elicits an immune response to human prostate-specific antigen (PSA) and wherein said active ingredient is selected from the group consisting of human PSA; and an expression system capable of generating in situ said human PSA.

2. The method of claim 1 wherein said active ingredient is human PSA.

3. The method of claim 1 wherein said expression system comprises DNA comprising a nucleotide sequence encoding said human PSA.

4. The method of claim 3 wherein said expression system is on expression vector for said human PSA.

5. The method of claim 1 wherein said active ingredient is formulated to be encapsulated in a liposome or coupled to a liposome and wherein said liposomes optionally contain an adjuvant or are precipitated with alum.

6. The method of claim 1 which further includes at least one adjuvant capable of enhancing said antitumor immune response.

7. The method of claim 6 wherein said adjuvant is selected from the group consisting of Freund's complete adjuvant; alum; lipid A; monophosphoryl lipid A; Bacillus Calmette-Guerin (BCG) or other bacteria polysaccharides; saponins; detoxified endotoxin (DETOX); muramyl tripeptide or muramyl dipeptide or their derivatives; SAF1; lymphokines; cytokines; colony stimulating factors; nonionic block copolymers; and immune stimulating complexes (ISCOMS).

8. The method of claim 1 wherein said subject is afflicted with metastatic prostate cancer; and/or wherein said subject has been surgically treated to excise said tumor but is at risk for recurrence.

* * * * *